United States Patent [19]

Nevel et al.

[11] Patent Number: 5,420,802
[45] Date of Patent: May 30, 1995

[54] SYSTEM AND METHOD FOR TESTING YARN ALTERING DEVICES

[75] Inventors: Avishai Nevel; John B. Lawson, both of Providence; Kendall W. Gordon, Jr., North Kingston, all of R.I.

[73] Assignee: Lawson-Hemphill, Inc., Central Falls, R.I.

[21] Appl. No.: 107,968

[22] Filed: Aug. 17, 1993

Related U.S. Application Data

[63] Continuation of Ser. No. 950,830, Sep. 24, 1992, abandoned.

[51] Int. Cl.$^6$ ............................................. D02G 3/00
[52] U.S. Cl. ................................. 364/551.01; 364/552
[58] Field of Search ................... 364/550, 551.01, 552; 57/264, 20; 358/107

[56] References Cited

U.S. PATENT DOCUMENTS

| | | | |
|---|---|---|---|
| 4,244,176 | 1/1981 | Shimizu et al. | 57/20 |
| 4,782,565 | 11/1988 | Sheehan et al. | 57/264 |
| 4,887,155 | 12/1989 | Massen | 358/107 |
| 4,891,974 | 1/1990 | Wassenhoven | 57/264 |
| 4,918,914 | 4/1990 | Eaton | 57/264 |
| 5,036,568 | 8/1991 | Goineau | 57/264 |
| 5,048,281 | 9/1991 | Dallmann et al. | 57/264 |

Primary Examiner—Ellis B. Ramirez
Assistant Examiner—Thomas Peeso
Attorney, Agent, or Firm—Brian M. Dingman

[57] ABSTRACT

A system and method for testing yarn altering devices in which the yarn is moved under precision yarn controls such as speed and tension, and then through the yarn altering device. Downstream of the yarn altering device the yarn is imaged, and from the image the widths of closely-spaced portions of the yarn are determined to establish the effect on the yarn of the yarn altering device.

18 Claims, 5 Drawing Sheets

SYSTEM AND METHOD FOR TESTING YARN ALTERING DEVICES

RELATED APPLICATION

This application is a continuation in part of application Ser. No. 07/950,830, filed on Sep. 24, 1992, abandoned.

FIELD OF INVENTION

This invention relates to a system and method for testing yarn altering devices such as entanglement jet devices and air texturing devices, in which the yarn is held at precise conditions as it is moved through the testing device, and images of the moving yarn are taken at closely spaced intervals with a CCD camera to capture and allow the analysis of a profile of a length of yarn so that the effect on the yarn of the yarn altering device may be determined.

BACKGROUND OF INVENTION

There are many types of yarn altering devices currently used in yarn production. Air operated devices include texturing devices that continuously tangle the yarn filaments to give the yarn more bulk, and entanglement devices that intermittently tangle or consolidate the filaments of multi-filament yarns so that the yarns may be more easily handled in future usages of the yarn such as in weaving and knitting. Other types of yarn altering devices that do not use air as the mechanical processing means include mechanical texturing devices, false twist devices, singeing or flame treating devices used to remove hairs, yarn brushing devices to increase the bulk by raising the hairs of a yarn, and yarn waxing devices that lubricate the yarns.

Such yarn altering devices are typically operated at very high speed and see extremely large amounts of yarn on a daily basis. Accordingly, the devices are subject to wear and breakdown. The integrity of these yarn altering devices and the other yarn handling systems in a manufacturing process are typically monitored by testing packages of yarn that have been processed through the production equipment. If there is a problem with the yarn on a package, the test personnel know that there is a problem with the equipment somewhere in the manufacturing process. However, it is then difficult to pinpoint the specific problem without being able to measure the performance of any yarn altering device within the production system.

When any yarn altering device in a production process is replaced, it of course may be the source of a problem. However, once the device is placed in production, there is really no means of easily pinpointing that that device is the source of a problem until the yarn produced is tested at a later time, and by that time large quantities of defective yarn may have been made.

SUMMARY OF INVENTION

It is therefore an object of this invention to provide a system and method for fully testing yarn altering devices either before or after they are put in production.

It is a further object of this invention to provide such a system and method which allows the establishment of quantitative operating criteria for yarn altering devices before they are placed in production to ensure good manufacturing results.

It is a further object of this invention to provide such a system and method which provides the ability to alter the operating parameters of the yarn altering device under test to pinpoint characteristics of operation.

This invention results from the realization that yarn altering devices such as air texturing jets and entanglement jets can be analyzed before or after their use in a production process by mounting the device on a test bed that applies precisely controlled conditions such as speed and/or tension to the yarn as it is pulled through the yarn altering device, and then imaging the yarn downstream of the yarn altering device to allow the test personnel to determine whether the yarn altering device has a desired effect on the yarn.

This invention features a system and method for testing yarn altering devices in which the yarn is moved first through the yarn altering device and then through a yarn imaging device. There are means for applying substantially constant conditions such as yarn speed and/or tension to the yarn as is passes through the yarn altering device, and means from determining, from the yarn imaging device, the widths of closely-spaced portions of the yarn to establish the effect on the yarn of the yarn altering device. The invention allows the operator to fully control the operating parameters of the yarn altering device, and image the yarn just downstream of the device to determine the performance characteristics of the device as well as how the device responds to changes in those controlled parameters.

The means for applying a substantially constant tension may include means for applying a controllable tension to the yarn before it enters the yarn altering device. The tension application may be accomplished by a biased pivoting arm over which the yarn travels before entering the yarn altering device. The yarn imaging device preferably includes a sensing array such as a linear CCD. The system may further include means for storing and/or displaying the determined widths for further and later analysis.

The yarn altering device under test may include an air operated device such as a yarn entanglement device or yarn texturing device. In that case, the system may further include means for adjusting the air pressure to the air operated device, and measuring the air flow rate to the device, to allow the parameters of operation to be altered to determine their effect on the yarn. The system may further include means for varying the yarn speed through the yarn altering device. The yarn altering device may be a yarn singeing device, a yarn brushing device, a yarn waxing device, or a yarn false twisting device. The yarn altering device has at least one operation parameter, and the system preferably further includes means for varying the parameters to allow observation of the effect of the parameters on the yarn.

The method of analyzing the performance of the yarn altering device contemplates moving the yarn through the yarn altering device, applying a substantially constant tension to the yarn upstream of the yarn altering device, and capturing the widths of closely-spaced portions of the moving yarn downstream of the yarn altering device to establish the effect on the yarn of the yarn altering device.

BRIEF DESCRIPTION OF THE DRAWINGS

Other objects, features, and advantages will occur to those skilled in the art from the following description of a preferred embodiment and the accompanying drawings in which.

DESCRIPTION OF THE PREFERRED EMBODIMENT

Figure 1:
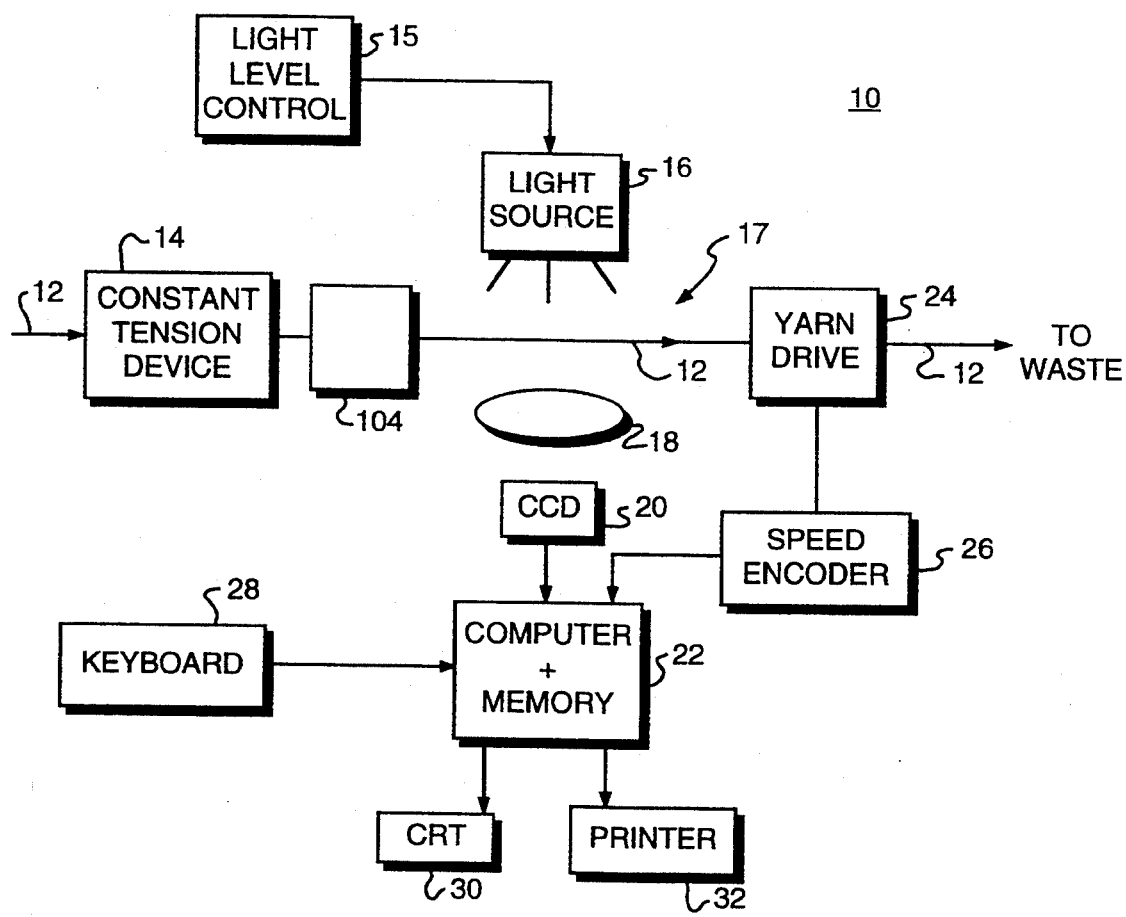
FIG. 1 is a schematic diagram of a yarn profile analyzer useful in the system and method according to this invention.

There is shown in FIG. 1 yarn profile analyzer 10 useful in the system and method of this invention. Analyzer 10 is used to make width or profile measurements of yarn 12 moved through imaging area 17 by yarn drive 24. Yarn 12 may pass through a constant tension device 14 before entering yarn altering device under test 104 on its way to an imaging area 17 so that it may be held under a constant, reproducible tension while being altered. Similar precision control is accomplished for yarn speed using yarn drive 24 so that the yarn may be passed through both the yarn altering device 104 and the imaging area 17 at a constant, reproducible speed. These controls provide the ability of device 10 to develop useful, accurate, quantitative data concerning each unit of yarn under test with the device, independent of any external equipment such as the machinery used to produce the yarn or any other production equipment. Light source 16 provides sufficient light in imaging area 17 so that the image focussed by lens 18 onto CCD array 20 is sharp enough for the desired purposes. Light level control 15 allows operator control of the light output level of light source 16. Preferably, light source 16 is an incandescent lamp, and control 15 is a regulated DC lamp power supply with variable output to provide a variable, steady light source without 60 Hz flicker. CCD 20 is preferably a linear CCD array having 2,048 pixels spaced on 13 micron centers. Lens 18 preferably magnifies the image four times so that a quarter-inch wide yarn fills the entire array, which is approximately one inch long. The amount of light sensed by each pixel of array 20 is provided as a related analog voltage at the output of array 20. This level can be compared to an adjustable, operator established threshold level in computer 22 so that the device reports a blocked unlighted pixel when only the selected percent of the maximum possible incipient light is received. For example, the device could be enabled to report blocked pixels when the received light is some percentage such as 20% less than the maximum light incident on the device with no yarn present in the measurement area. This threshold level combined with the speed can either emphasize or filter out specific details of a yarn such as hairiness. Other details of the light source regulation and threshold level setting are disclosed in application Ser. No. 07/950,830, incorporated herein by reference.

Encoder 26 is preferably used to measure the lengths of yarn transported by drive mechanism 24, which is then translated into yarn lengths and then yarn speed by computer 22. Keyboard 28 is used by the operator to enter commands for operation of computer 22 in a known fashion. The output of the device may then be applied to either CRT 30 or printer 32 as desired and explained more fully below.

Figure 2A:
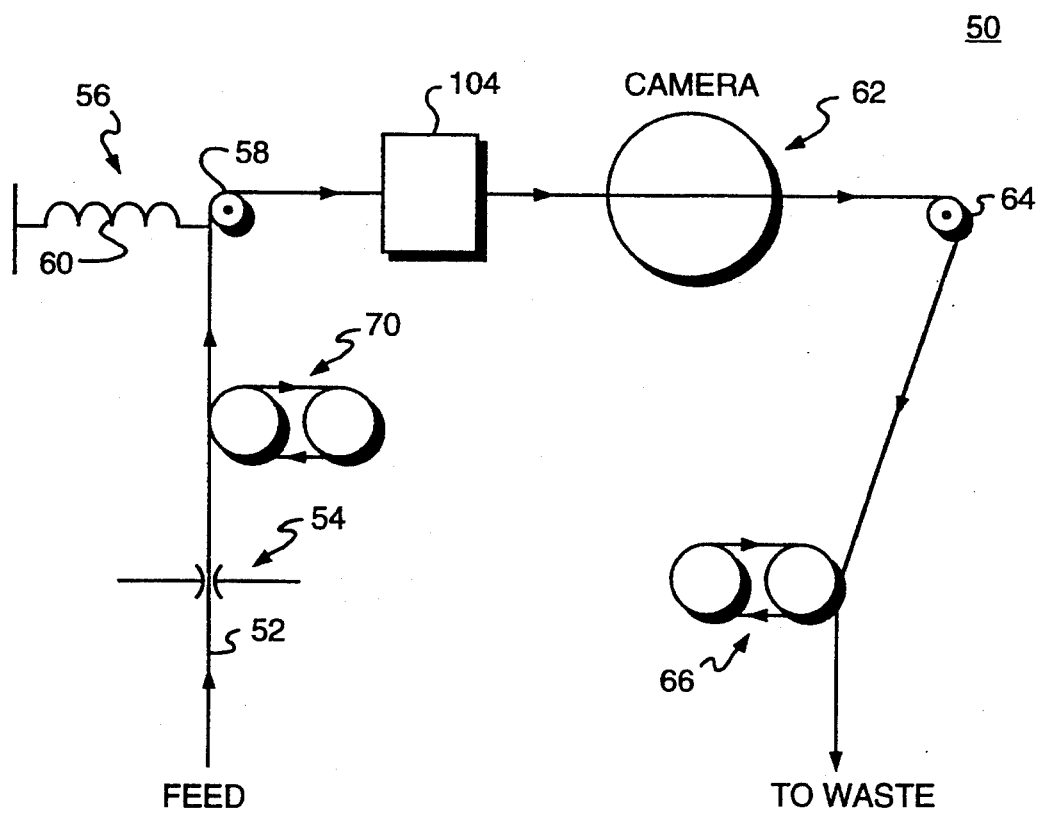
FIG. 2A is a highly schematic view of a preferred embodiment of the analyzer of FIG. 1.

Embodiment 50 of the yarn profile analyzer useful for practicing this invention is shown very schematically in FIG. 2A. Yarn 52 preferably drawn off a yarn package is sent through pretension device 54, around a first set of driven feed rolls 70, and then through constant tension device 56 schematically depicted as roller 58 and adjustable tension spring 60. Device 56 preferably allows the operator to select the tension applied to yarn 52 from ½ to 750 grams. The yarn then passes through yarn altering device 104, and then to camera 62 which images the yarn and provides the image to the computer. In a preferred embodiment, the linear CCD array described above is employed and operated at about 3,200 scans per second with 15,000 yarn diameters measured and stored for selected lengths of yarn with the yarn running at selected speeds. This is accomplished with a clock running at approximately 15 megahertz. The yarn is then directed by roller 64 to driven roll pair 66 around which yarn 52 is wound one or more times to pull the yarn through camera 62.

Figure 2B:
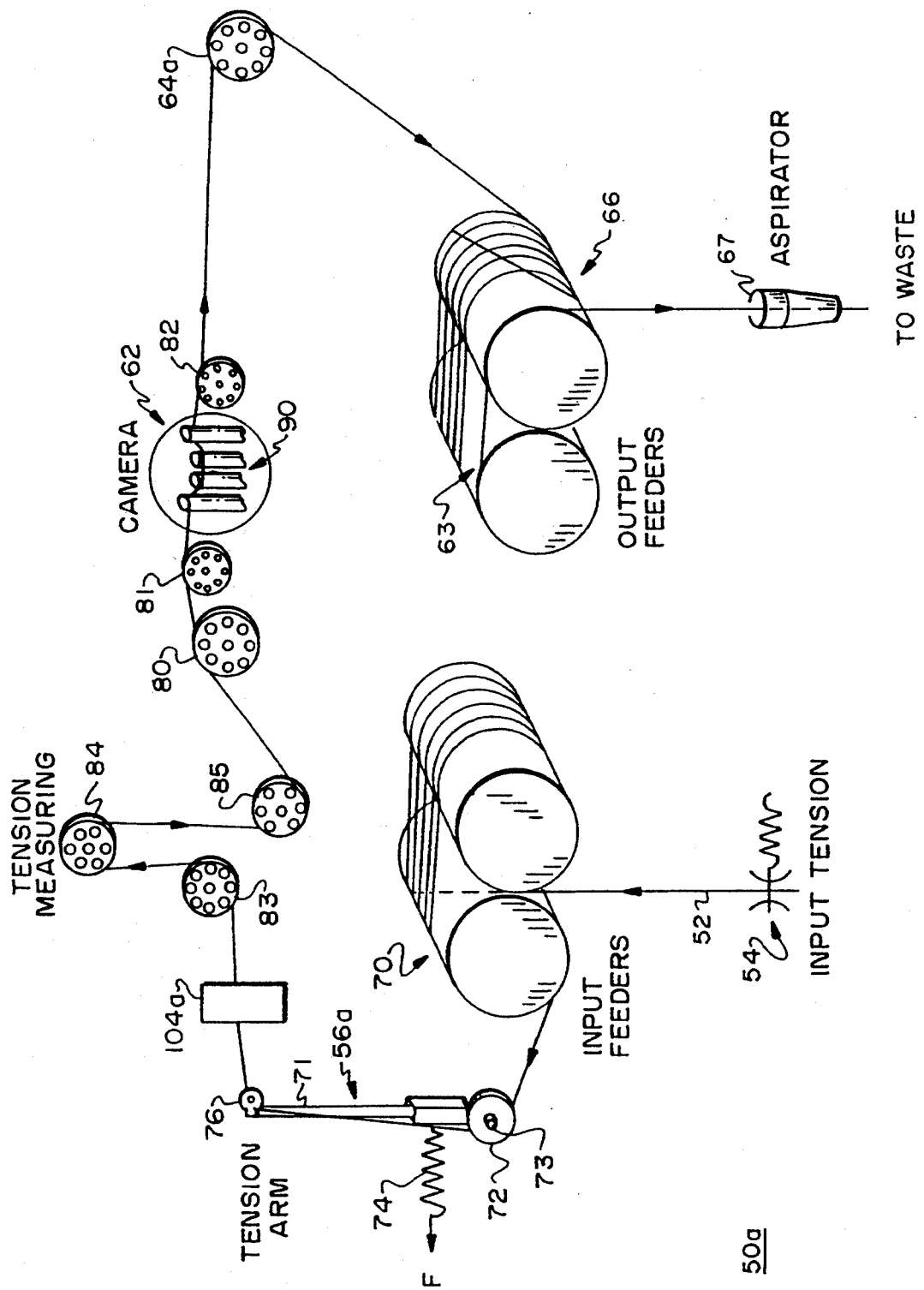
FIG. 2B is a more detailed schematic view of the analyzer of FIG. 2A.

A preferred embodiment showing one application of system 50a is shown in more detail in FIG. 2B. Input tension device 54 may be a standard tension device to provide a small tension against which input feed roll pair 70 pulls. The yarn is wrapped around roll pair 70 a number of times and then travels over constant tension device 71 that may be the type of adjustable constant tension arm shown in U.S. Pat. No. 3,575,360, which consists of tension arm 56a pivoting on point 73, to which is applied a force in the direction of arrow F by adjustable tension spring 74. Top roller 76 applies the tension to the yarn and directs it to the yarn altering device under test 104a. The tension coming out of device 104a is measured in a tensiometer depicted as rollers 83 through 85 as is known in the art so that any changes in tension due to the yarn passing through device 104a are measured. The yarn is then provided tip to rollers 80 through 82 for imaging by camera 62, by output roll pair 66 that pulls the yarn through device 104a through the tension measurement and camera 62 at a controllable, adjustable velocity. The yarn is then moved to waste by air aspirator 67. Yarn guide 90 is used in the yarn measurement area to make sure the yarn is centered within the measurement area and also to flatten out the yarn to make a better presentation of the yarn to the camera.

Figure 3C:
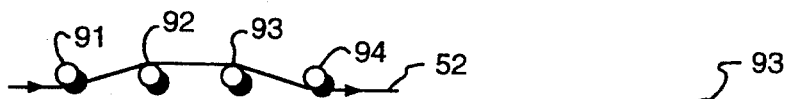
FIGS. 3A through 3C are front, side and top views, respectively, of the yarn centering and flattening device of the analyzer of FIG. 2B.
Figure 3B:
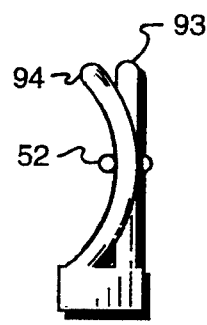
Figure 3A:
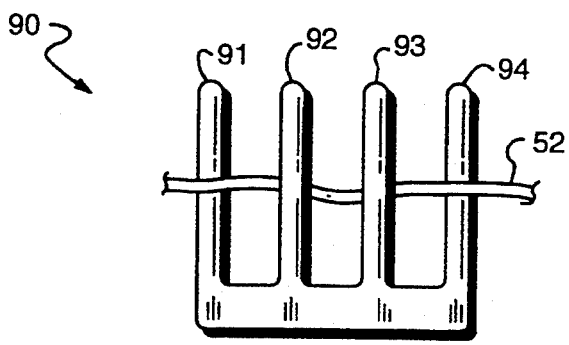

Device 90 is shown in more detail in FIGS. 3A through 3C. The device includes two "C" shaped fingers 91 and 94 offset from straight center fingers 92 and 93 to create a "C" shaped path for the yarn to traverse so that the yarn is pulled over the edges of the fingers to flatten and spread the yarn slightly so that it presents a better, flatter profile in the measurement zone, preferably between fingers 92 and 93. Other guides include V-groove device, or a pin over which the yarn may be pulled.

In conjunction with the variable light level and variable CCD pixel threshold, the device is enabled to detect loops and hairs to a desired level so that relatively gross or relatively fine measurements can be made of the yarn profile or diameter. Also contributing to this measurement sensitivity is the use of the system in a manner in which the measured diameter of the yarn is taken as the greatest distance between blocked sensing array pixels. Accordingly, a hair or loop in the yarn passing in front of the array will cause the measurement of a larger yarn profile (diameter), even if there is a gap between the main body of the yarn and the loop. Thus, the device truly measures the total yarn width at the point of measurement.

Figure 4:
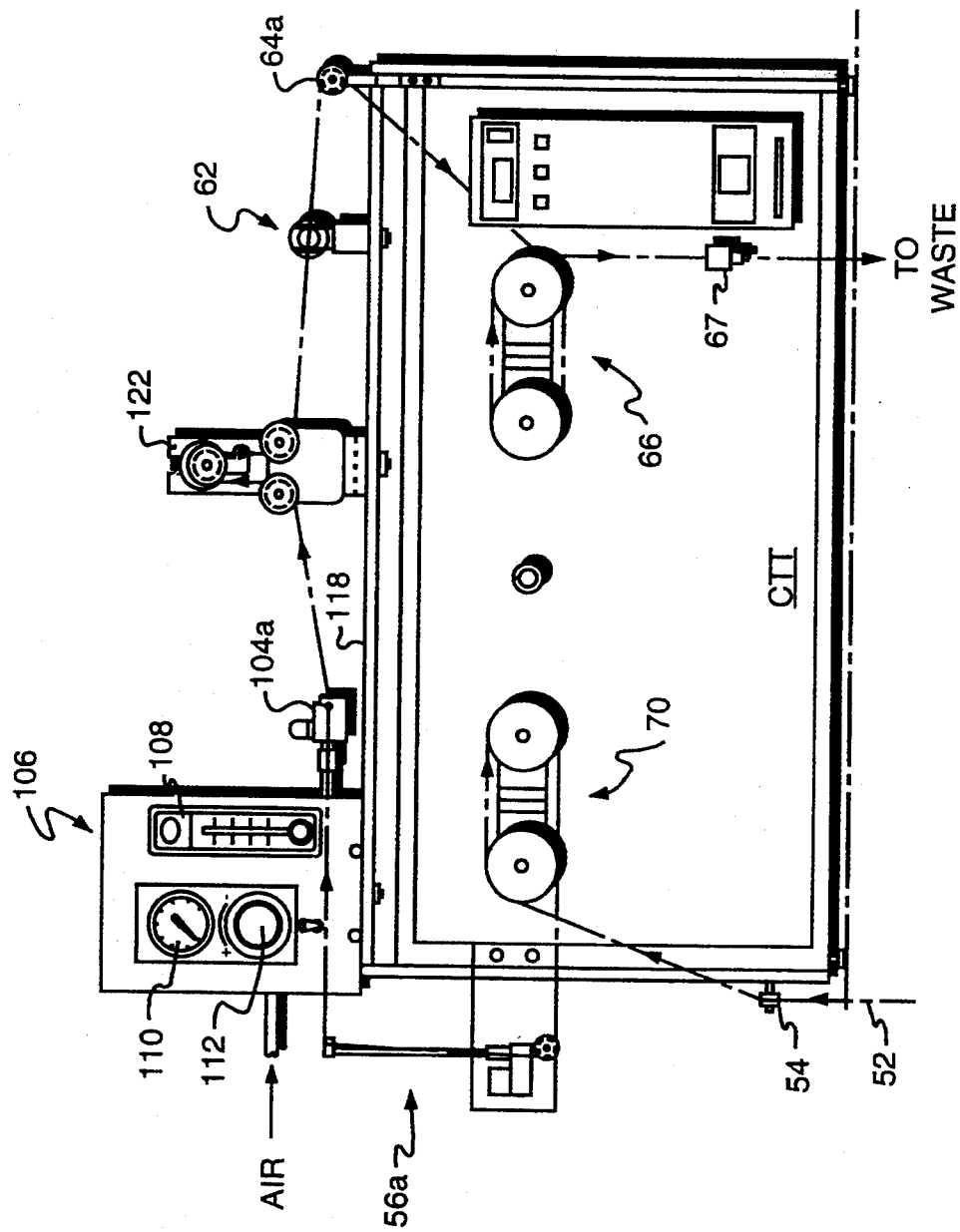
FIG. 4 is a front view of the complete yarn altering device test system of this invention employing the analyzer of FIGS. 1 through 3.

This invention employs the yarn analyzer detailed in FIGS. 1 through 3 in a test bed that provides for the mounting of the yarn altering device to be tested downstream of tension arm 56a and upstream of measurement area 62, FIG. 4. The device under test 104a is placed in the path of yarn flow 52 in the same manner as the device would be used in production so that quantitative tests may be performed on the device using the analyzer. In this example, device 104a is an air-operated yarn altering device such as an air entanglement unit. Device 104a is mounted to air control panel 106 that is itself mounted to the top of cabinet 118 holding the yarn drive and tension application devices, as well as the camera for imaging the yarn. Tensiometer 122 measures the yarn tension to determine changes in tension occurring as a result of changes of controls on the yarn altering device. For air entangling devices such as this, there is included air flow meter 108 and air pressure readout 110. The pressure of the air provided to device 104 is controlled by turning knob 112 to increase or decrease pressure as indicated on meter 110. The air first flows through flow measuring device 108 which includes an adjustable orifice for adjusting the flow rate so that both the air pressure and flow rate to device 104a may be altered for creating desired operation conditions at yarn altering device 104a. In conjunction with the adjustable constant tension device 56a and the adjustable speed drive of this invention, the test bed allows the operator to vary a number of operation parameters to test their effect on the yarn in order to determine whether device 104a is of sufficient quality to be used in a production environment, or to determine optimum operating parameters for the device.

This invention is not limited to the use of an air operated yarn altering device. Other yarn altering devices, for example a false twisting device, a flame treating or singeing device to remove yarn hairs, a yarn brushing device, a yarn waxing device, or other yarn altering devices may be mounted to cabinet 118. The test bed is then provided with the ability to alter desired parameters of operation of the yarn altering device under test so that the device can be fully tested and evaluated as desired. The precise constant tension and/or speed controls, in conjunction with the yarn width measuring system of this invention, then allows an accurate profile of the yarn to be assembled for analysis to determine the effect of each operating parameter on the yarn.

Figure 5:
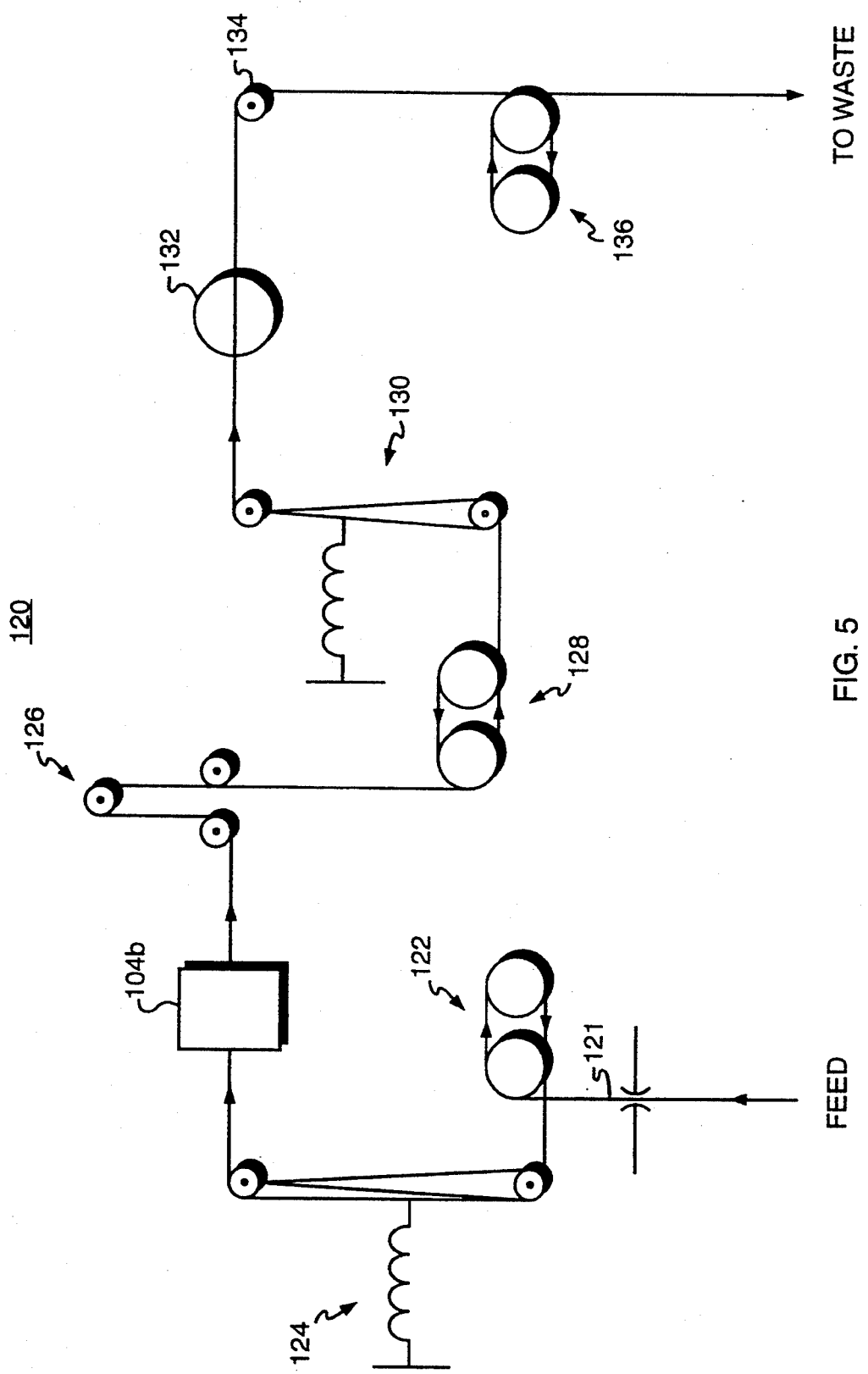
FIG. 5 is a schematic diagram of an alternative setup for testing a false twisting device.

One example of a set up for testing other yarn altering devices is shown in FIG. 5 in which false twisting device 104b is shown in test set tip 120. False twist device 104b typically includes a heater with a false-twister such as a friction disc drive type false twister just downstream of the heater. In this application, one of the variables is the input pretension as well as the tension in the camera zone. To accomplish this, the yarn runs through a pretension device 121 and then over driven roll pair 122 and then over first tension arm 124. The speed of rolls 122 is controlled by the tension setting of arm 124 as is known in the art to maintain a constant tension in the false twister. The tension is measured with tensiometer 126. The yarn is then wrapped around second driven roll pair 128 that is driven at a selected speed to pull the yarn through the false twister at a selected speed. The yarn then passes over second tension application arm 130 which in a similar fashion to the first arm also is adapted to control the speed of driven roll pair 136 to provide a constant tension and speed through camera 132. Pulley 134 guides the yarn from camera 132 to rolls 136.

A partial listing of yarn altering devices that could be subject of this invention are as follows:

| Device | Required Input Controls and Data | Measurement to be Made |
| --- | --- | --- |
| Air Entanglement | Input Tension<br>Yarn Speed<br>Air Pressure | Air Flow<br>Output Tension<br>Entanglement Count<br>Profile of Balloon and<br>Entanglement Diameters |
| Air Texturing | Input tension<br>Yarn speed<br>Air pressure<br>Water flow | Air flow<br>Output tension<br>Profile of loops<br>Counts of loops at<br>various threshold levels |
| Singeing | Yarn speed<br>Flame<br>Closeness<br>Length<br>Intensity (gas flow) | Hair counts at various<br>thresholds<br>Overall profile<br>appearance |
| Yarn Brushing | Input tension<br>Speed of yarn<br>Brush<br>Design (construction)<br>Speed<br>Bristle type<br>Yarn path and wrap on brush | Hair counts at various<br>threshold levels<br>Overall profile<br>appearance |
| Yarn Waxing | Yarn speed<br>Wax type<br>Pressure and/or<br>speed of wax drive<br>Input tension | Hairiness at various<br>thresholds<br>Output tension<br>General profile<br>appearance |
| False Twisting | Input pretension<br>Input camera tension<br>Speed of yarn<br>False twister<br>Speed<br>Number of disks<br>Type of disks<br>Heater temperature and length<br>Type of heater contact | Profile qualify<br>Bulk (mean diameter) |

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A system for testing yarn altering devices, comprising:
    a yarn altering device;
    a yarn imaging device;
    means for moving yarn first through said yarn altering device and then through said imaging device at a controlled speed;
    means for applying a controllable tension to the yarn just upstream of said yarn altering device; and
    means for measuring, using said yarn imaging device, the widths of closely-spaced portions of the yarn passed through the imaging device to establish an effect on the yarn of the yarn altering device to allow an evaluation of the effectiveness of the yarn altering device.

2. The system of claim 1 in which said means for applying a controllable tension includes a biased pivoting arm over which the yarn travels before entering the yarn altering device.

3. The system of claim 1 in which said yarn imaging device includes an array of light-sensing elements.

4. The system of claim 1 further including means for storing the determined widths.

5. The system of claim 1 further including means for displaying the determined widths.

6. The system of claim 1 in which said yarn altering device includes an air operated device.

7. The system of claim 1 in which said yarn altering device is a yarn brushing device.

8. The system of claim 6 in which said air operated device is a yarn entanglement device.

9. The system of claim 6 in which said air operated device is a yarn texturing device.

10. The system of claim 6 further including means for adjusting the air pressure to said air operated device.

11. The system of claim 6 further including means for measuring the air flow to said air operated device.

12. The system of claim 1 in which said means for moving includes means for establishing a desired yarn speed through said yarn altering device.

13. The system of claim 1 in which said yarn altering device is a yarn singeing device.

14. The system of claim 1 in which said yarn altering device is a yarn waxing device.

15. The system of claim 1 in which said yarn altering device is a yarn false twisting device.

16. The system of claim 1 in which said yarn altering device has at least one operation parameter, and said system further includes means for varying said parameter to allow observation of the effect of the parameter on the yarn.

17. The system of claim 1 further including means for measuring yarn tension just downstream of said yarn altering device to determine tension changes caused by said yarn altering device.

18. A system for testing an air operated yarn altering device, comprising:
   means for controlling the yarn speed through the system;
   a precision tension device for applying a substantially constant tension to the yarn upstream of the yarn altering device;
   means for controlling the pressure and measuring the flow of air to the yarn altering device to change the operation parameters; and
   a yarn imaging camera downstream of the yarn altering device for capturing images of closely-spaced portions of the moving yarn to allow analysis of the effect on the yarn of the yarn altering device for testing of the air operated yarn altering device.

* * * * *